(12) United States Patent
Colburn et al.

(10) Patent No.: US 7,950,393 B2
(45) Date of Patent: May 31, 2011

(54) ENDOTRACHEAL CUFF AND TECHNIQUE FOR USING THE SAME

(75) Inventors: Joel C. Colburn, Walnut Creek, CA (US); Donald S. Nelson, San Ramon, CA (US); Paul W. Martens, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1028 days.

(21) Appl. No.: 11/540,247

(22) Filed: Sep. 29, 2006

(65) Prior Publication Data

US 2008/0142016 A1 Jun. 19, 2008

(51) Int. Cl.
*A61M 11/00* (2006.01)
(52) U.S. Cl. .................. 128/207.15; 606/194
(58) Field of Classification Search ........ 128/207.14–207.18, 207.29; 606/108, 606/194–195; 600/184; 604/96.01
See application file for complete search history.

(56) References Cited

U.S. PATENT DOCUMENTS

| | | | |
|---|---|---|---|
| 2,927,584 A | 3/1960 | Wallace | |
| 3,769,983 A | 11/1973 | Merav | |
| 3,810,474 A | 5/1974 | Cross | |
| 3,822,238 A | 7/1974 | Blair et al. | |
| 3,913,565 A | 10/1975 | Kawahara | |
| 3,971,385 A | 7/1976 | Corbett | |
| 3,975,350 A | 8/1976 | Hudgin et al. | |
| 3,995,643 A | 12/1976 | Merav | |
| 4,022,217 A | 5/1977 | Rowean | |
| 4,106,509 A | * | 8/1978 | McWhorter ........ 604/129 |
| 4,130,617 A | 12/1978 | Wallace | |
| 4,230,108 A | 10/1980 | Young | |
| 4,231,365 A | 11/1980 | Scarberry | |
| 4,235,239 A | 11/1980 | Elam | |
| 4,340,046 A | 7/1982 | Cox | |
| 4,569,344 A | 2/1986 | Palmer | |
| 4,638,539 A | 1/1987 | Palmer | |
| 4,649,913 A | 3/1987 | Watson | |
| 4,696,296 A | 9/1987 | Palmer | |
| 4,700,700 A | 10/1987 | Eliachar | |
| 4,791,920 A | 12/1988 | Fauza | |
| 4,825,859 A | 5/1989 | Lambert | |
| 4,825,861 A | 5/1989 | Koss | |
| 4,834,726 A | 5/1989 | Lambert | |
| 4,836,199 A | 6/1989 | Palmer | |
| 4,838,255 A | 6/1989 | Lambert | |

(Continued)

FOREIGN PATENT DOCUMENTS

CA 2353007 6/2000

(Continued)

OTHER PUBLICATIONS

U.S. Appl. No. 11/472,733, filed Jun. 22, 2006, Nelson.

(Continued)

*Primary Examiner* — Steven O Douglas
(74) *Attorney, Agent, or Firm* — Fletcher Yoder

(57) ABSTRACT

An inflatable balloon cuff associated with a tracheal tube may be adapted to filter microbial secretions and reduce their passage into the lungs. A cuff as provided may include a cross-linked polymeric structure that may serve to exclude certain secretions on the basis of size. The polymeric structure may be incorporated onto all or part of the surface of the inflatable balloon cuff.

25 Claims, 4 Drawing Sheets

U.S. PATENT DOCUMENTS

| | | | |
|---|---|---|---|
| 4,850,348 A | 7/1989 | Pell et al. | |
| 4,867,153 A | 9/1989 | Lorenzen et al. | |
| 4,872,579 A | 10/1989 | Palmer | |
| 4,886,059 A | 12/1989 | Weber | |
| 4,927,412 A | 5/1990 | Menasche | |
| 4,938,741 A | 7/1990 | Lambert | |
| 4,963,313 A | 10/1990 | Noddin et al. | |
| 4,967,743 A | 11/1990 | Lambert | |
| 4,979,505 A | 12/1990 | Cox | |
| 5,020,534 A | 6/1991 | Pell et al. | |
| 5,021,045 A | 6/1991 | Buckberg et al. | |
| 5,025,806 A | 6/1991 | Palmer et al. | |
| 5,029,580 A | 7/1991 | Radford et al. | |
| 5,033,466 A | 7/1991 | Weymuller, Jr. | |
| 5,060,646 A | 10/1991 | Page | |
| 5,065,754 A | 11/1991 | Jensen | |
| 5,074,840 A | 12/1991 | Yoon | |
| 5,076,268 A | 12/1991 | Weber | |
| 5,098,379 A | 3/1992 | Conway et al. | |
| 5,103,816 A | 4/1992 | Kirschbaum et al. | |
| 5,107,829 A | 4/1992 | Lambert | |
| 5,120,322 A | 6/1992 | Davis et al. | |
| 5,122,122 A | 6/1992 | Allgood | |
| 5,133,345 A | 7/1992 | Lambert | |
| 5,135,516 A | 8/1992 | Sahatjian et al. | |
| 5,137,671 A | 8/1992 | Conway et al. | |
| 5,158,569 A | 10/1992 | Strickland et al. | |
| 5,165,420 A | 11/1992 | Strickland | |
| 5,176,638 A | 1/1993 | Don Michael | |
| 5,190,810 A | 3/1993 | Kirschbaum et al. | |
| 5,199,427 A | 4/1993 | Strickland | |
| 5,201,310 A | 4/1993 | Turnbull et al. | |
| 5,207,643 A | 5/1993 | Davis | |
| 5,213,576 A * | 5/1993 | Abiuso et al. | 604/103.01 |
| 5,215,522 A | 6/1993 | Page et al. | |
| 5,218,957 A | 6/1993 | Strickland | |
| 5,230,332 A | 7/1993 | Strickland | |
| 5,233,979 A | 8/1993 | Strickland | |
| 5,246,012 A | 9/1993 | Strickland | |
| 5,250,070 A | 10/1993 | Parodi | |
| 5,251,619 A | 10/1993 | Lee | |
| 5,261,896 A | 11/1993 | Conway et al. | |
| 5,263,478 A | 11/1993 | Davis | |
| 5,269,770 A | 12/1993 | Conway et al. | |
| 5,277,177 A | 1/1994 | Page et al. | |
| 5,290,585 A | 3/1994 | Elton | |
| 5,304,121 A | 4/1994 | Sahatjian | |
| 5,331,027 A | 7/1994 | Whitbourne | |
| 5,360,402 A | 11/1994 | Conway et al. | |
| 5,370,656 A | 12/1994 | Shevel | |
| 5,370,899 A | 12/1994 | Conway et al. | |
| 5,374,261 A | 12/1994 | Yoon | |
| 5,392,787 A | 2/1995 | Yoon | |
| 5,397,302 A | 3/1995 | Weaver et al. | |
| 5,407,423 A | 4/1995 | Yoon | |
| 5,417,671 A | 5/1995 | Jackson | |
| 5,423,745 A | 6/1995 | Todd et al. | |
| 5,439,457 A | 8/1995 | Yoon | |
| 5,443,063 A | 8/1995 | Greenberg | |
| 5,447,505 A | 9/1995 | Valentine et al. | |
| 5,451,204 A | 9/1995 | Yoon | |
| 5,466,231 A | 11/1995 | Cercone et al. | |
| 5,469,864 A | 11/1995 | Rosenblatt | |
| 5,482,740 A | 1/1996 | Conway et al. | |
| 5,484,426 A | 1/1996 | Yoon | |
| 5,487,730 A | 1/1996 | Marcadis et al. | |
| 5,494,029 A | 2/1996 | Lane et al. | |
| 5,501,669 A | 3/1996 | Conway et al. | |
| 5,507,284 A | 4/1996 | Daneshvar | |
| 5,509,899 A | 4/1996 | Fan et al. | |
| 5,524,642 A | 6/1996 | Rosenblatt | |
| 5,545,132 A | 8/1996 | Fagan et al. | |
| 5,556,391 A | 9/1996 | Cercone et al. | |
| 5,593,718 A | 1/1997 | Conway et al. | |
| 5,599,292 A | 2/1997 | Yoon | |
| 5,599,299 A | 2/1997 | Weaver et al. | |
| 5,599,321 A | 2/1997 | Conway et al. | |
| 5,611,336 A | 3/1997 | Page et al. | |
| 5,613,950 A | 3/1997 | Yoon | |
| 5,649,902 A | 7/1997 | Yoon | |
| 5,653,229 A | 8/1997 | Greenberg | |
| 5,670,111 A | 9/1997 | Conway et al. | |
| 5,674,192 A | 10/1997 | Sahatjian et al. | |
| 5,693,014 A | 12/1997 | Abele et al. | |
| 5,694,922 A | 12/1997 | Palmer | |
| 5,697,365 A | 12/1997 | Pell | |
| 5,700,239 A | 12/1997 | Yoon | |
| 5,715,815 A | 2/1998 | Lorenzen et al. | |
| 5,720,726 A | 2/1998 | Marcadis et al. | |
| 5,722,931 A | 3/1998 | Heaven | |
| 5,730,123 A | 3/1998 | Lorenzen | |
| 5,733,252 A | 3/1998 | Yoon | |
| 5,735,271 A | 4/1998 | Lorenzen et al. | |
| 5,765,559 A | 6/1998 | Kim | |
| 5,769,882 A | 6/1998 | Fogarty et al. | |
| 5,810,786 A | 9/1998 | Jackson et al. | |
| 5,819,723 A * | 10/1998 | Joseph | 128/207.14 |
| 5,819,733 A | 10/1998 | Bertram | |
| 5,827,215 A | 10/1998 | Yoon | |
| 5,843,017 A | 12/1998 | Yoon | |
| 5,843,028 A | 12/1998 | Weaver et al. | |
| 5,843,060 A | 12/1998 | Cercone | |
| 5,843,089 A | 12/1998 | Sahatjian et al. | |
| 5,868,719 A | 2/1999 | Tsukernik | |
| 5,908,406 A | 6/1999 | Ostapchenko | |
| 5,951,597 A | 9/1999 | Westlund et al. | |
| 5,954,706 A | 9/1999 | Sahatjian | |
| 5,954,740 A | 9/1999 | Ravenscroft et al. | |
| 5,971,954 A | 10/1999 | Conway et al. | |
| 5,976,072 A | 11/1999 | Greenberg | |
| 5,997,503 A | 12/1999 | Willis et al. | |
| 5,997,546 A | 12/1999 | Foster et al. | |
| 6,010,480 A | 1/2000 | Abele et al. | |
| 6,012,451 A | 1/2000 | Palmer | |
| 6,048,332 A | 4/2000 | Duffy et al. | |
| 6,110,192 A | 8/2000 | Ravenscroft et al. | |
| 6,120,904 A * | 9/2000 | Hostettler et al. | 428/423.3 |
| 6,129,547 A | 10/2000 | Cise | |
| 6,152,136 A | 11/2000 | Pagan | |
| 6,169,123 B1 | 1/2001 | Cercone | |
| 6,210,364 B1 | 4/2001 | Anderson et al. | |
| 6,214,895 B1 | 4/2001 | Cercone | |
| 6,227,200 B1 | 5/2001 | Crump et al. | |
| 6,240,321 B1 | 5/2001 | Janke et al. | |
| 6,248,088 B1 | 6/2001 | Yoon | |
| 6,264,631 B1 | 7/2001 | Willis et al. | |
| 6,264,633 B1 | 7/2001 | Knorig | |
| 6,277,089 B1 | 8/2001 | Yoon | |
| 6,312,421 B1 | 11/2001 | Boock | |
| 6,322,586 B1 | 11/2001 | Monroe et al. | |
| 6,364,856 B1 | 4/2002 | Ding et al. | |
| 6,378,521 B1 | 4/2002 | Van Den Berg | |
| 6,394,093 B1 | 5/2002 | Lethi | |
| 6,395,012 B1 | 5/2002 | Yoon et al. | |
| 6,398,266 B1 | 6/2002 | Crump | |
| 6,409,716 B1 | 6/2002 | Sahatjian et al. | |
| 6,481,436 B1 | 11/2002 | Neame | |
| 6,494,203 B1 | 12/2002 | Palmer | |
| 6,524,274 B1 | 2/2003 | Rosenthal et al. | |
| 6,526,977 B1 | 3/2003 | Göbel | |
| 6,537,194 B1 * | 3/2003 | Winkler | 600/3 |
| 6,543,451 B1 | 4/2003 | Crump et al. | |
| 6,551,272 B2 | 4/2003 | Gobel | |
| 6,572,813 B1 | 6/2003 | Zhang et al. | |
| 6,584,970 B1 | 7/2003 | Crump et al. | |
| 6,588,425 B2 | 7/2003 | Rouns et al. | |
| 6,588,427 B1 | 7/2003 | Carlsen et al. | |
| 6,602,218 B2 | 8/2003 | Yoon | |
| 6,602,219 B2 | 8/2003 | Madsen et al. | |
| 6,609,520 B1 | 8/2003 | Carlsen et al. | |
| 6,612,304 B1 | 9/2003 | Cise et al. | |
| 6,612,305 B2 | 9/2003 | Fauza | |
| 6,613,025 B1 | 9/2003 | Palasis | |
| 6,615,835 B1 | 9/2003 | Cise et al. | |
| 6,620,128 B1 | 9/2003 | Simhambhatla | |
| 6,623,450 B1 | 9/2003 | Dutta | |
| 6,629,530 B2 | 10/2003 | Cise | |

| | | | | | | |
|---|---|---|---|---|---|---|
| 6,632,091 | B1 | 10/2003 | Cise et al. | 2005/0038381 A1 | 2/2005 | McMichael |
| 6,651,664 | B1 | 11/2003 | Lomholt | 2005/0065468 A1 | 3/2005 | Goebel |
| 6,688,306 | B1 | 2/2004 | Cise et al. | 2005/0124932 A1 | 6/2005 | Foster et al. |
| 6,698,424 | B2 | 3/2004 | Madsen et al. | 2005/0124935 A1 | 6/2005 | McMichael |
| 6,705,320 | B1 | 3/2004 | Anderson | 2005/0137619 A1 | 6/2005 | Schewe et al. |
| 6,722,368 | B1 | 4/2004 | Shaikh | 2005/0166924 A1 | 8/2005 | Thomas et al. |
| 6,726,696 | B1 | 4/2004 | Houser et al. | | | |
| 6,745,773 | B1 | 6/2004 | Gobel | | | |
| 6,767,340 | B2 | 7/2004 | Willis et al. | | | |
| 6,769,430 | B1 | 8/2004 | Carlsen et al. | | | |
| 6,770,066 | B1 | 8/2004 | Weaver et al. | | | |
| 6,786,876 | B2 | 9/2004 | Cox | | | |
| 6,790,221 | B2 | 9/2004 | Monroe et al. | | | |
| 6,796,309 | B2 | 9/2004 | Nash et al. | | | |
| 6,802,317 | B2 | 10/2004 | Göbel | | | |
| 6,805,125 | B1 | 10/2004 | Crump et al. | | | |
| 6,808,521 | B1 | 10/2004 | McMichael | | | |
| 6,814,730 | B2 | 11/2004 | Li | | | |
| 6,890,339 | B2 | 5/2005 | Sahatjian et al. | | | |
| 6,908,449 | B2 | 6/2005 | Willis et al. | | | |
| 6,916,307 | B2 | 7/2005 | Willis et al. | | | |
| 6,923,786 | B2 | 8/2005 | Rouns et al. | | | |
| 6,997,909 | B2 | 2/2006 | Goldberg | | | |
| 7,040,321 | B2 | 5/2006 | Gobel | | | |
| 7,040,322 | B2 | 5/2006 | Fortuna | | | |
| 7,066,905 | B2 | 6/2006 | Squire et al. | | | |
| 7,098,028 | B2 | 8/2006 | Holmes et al. | | | |
| 7,147,252 | B2 | 12/2006 | Teuscher et al. | | | |
| 7,258,120 | B2 | 8/2007 | Melker | | | |
| 2002/0032407 | A1 | 3/2002 | Willis et al. | | | |
| 2002/0082552 | A1 | 6/2002 | Ding et al. | | | |
| 2002/0195110 | A1 | 12/2002 | Watton | | | |
| 2003/0073625 | A1* | 4/2003 | Redman et al. ............ 514/12 | | | |
| 2003/0116162 | A1 | 6/2003 | Madsen et al. | | | |
| 2003/0225369 | A1 | 12/2003 | McMichael et al. | | | |
| 2003/0225392 | A1 | 12/2003 | McMichael et al. | | | |
| 2003/0225393 | A1 | 12/2003 | McMichael et al. | | | |
| 2004/0079376 | A1* | 4/2004 | Melker ............... 128/207.14 | | | |
| 2004/0106899 | A1 | 6/2004 | McMichael et al. | | | |
| 2004/0106900 | A1 | 6/2004 | Triebes et al. | | | |
| 2004/0106901 | A1 | 6/2004 | Letson et al. | | | |
| 2004/0116898 | A1 | 6/2004 | Hawk | | | |
| 2004/0154623 | A1 | 8/2004 | Schaeffer et al. | | | |
| 2004/0193100 | A1 | 9/2004 | Van Hooser et al. | | | |
| 2004/0193101 | A1 | 9/2004 | Van Hooser et al. | | | |
| 2004/0215142 | A1 | 10/2004 | Matheis et al. | | | |
| 2004/0221853 | A1 | 11/2004 | Miller | | | |
| 2004/0255951 | A1 | 12/2004 | Grey | | | |
| 2005/0004560 | A1 | 1/2005 | Cox | | | |
| 2005/0033267 | A1 | 2/2005 | Decaria | | | |
| 2005/0033268 | A1 | 2/2005 | Decaria | | | |
| 2005/0033269 | A1 | 2/2005 | Decaria | | | |

FOREIGN PATENT DOCUMENTS

| | | |
|---|---|---|
| DE | 19500550 | 7/1996 |
| DE | 19855521 | 6/2000 |
| EP | 0884061 | 6/1998 |
| EP | 1267981 | 4/2000 |
| EP | 1005877 | 6/2000 |
| EP | 1135184 | 6/2000 |
| GB | 2168256 | 6/1986 |
| WO | WO 95/22367 | 8/1995 |
| WO | WO 00/27461 | 5/2000 |
| WO | WO 00/32262 | 6/2000 |
| WO | WO 00/32263 | 6/2000 |
| WO | WO 03/045487 | 6/2003 |
| WO | WO 2004/067262 | 8/2004 |
| WO | WO 2004/101046 | 11/2004 |
| WO | WO 2006/023486 | 3/2006 |

OTHER PUBLICATIONS

U.S. Appl. No. 11/472,915, filed Jun. 22, 2006, Morris et al.
U.S. Appl. No. 11/473,285, filed Jun. 22, 2006, Colburn et al.
U.S. Appl. No. 11/473,362, filed Jun. 22, 2006, Nelson.
U.S. Appl. No. 11/529,117, filed Sep. 28, 2006, Martens et al.
Blunt, Mark C. Gel Lubrication of the Tracheal Tube Cuff Reduces Pulmonary Aspiration, Anesthesiology, Aug. 2001, pp. 377-381, vol. 95, No. 2.
Dullenkopf, et al., "Fluid leakage past tracheal tube cuffs: evaluation on the new Microcuff endotracheal tube," *Intensive Care Medicine*, (2003) vol. 29, pp. 1849-1853.
Tecogel brochure, Noveon Thermedics Polymer Products, Oct. 2003.
Ayşe Gönen Karakeçili et al.; "Comparison of Bacterial and Tissue Cell Initial Adhesion on Hydrophilic/Hydrophobic Biomaterials," J Biomater. Sci. Polymer Edn, vol. 13, No. 2, pp. 185-196 (2002).
Blunt et al.; "Gel Lubrication of the Tracheal Tube Cuff Reduces Pulmonary Aspiration," 2001 American Society of Anesthesiologists, Inc. Lippincott Williams & Wilkins, Inc.; Anesthesiology, V. 95, No. 2, Aug. 2001.
Shintani; "Modification of Medical Device Surface to Attain Anti-Infection," National Institute of Health Sciences; Trends Biomater. Artif. Organs, vol. 18(1), pp. 1-8 (2004).
Sartomer Application Bulletin; "Functional Acrylic Monomers as Modifiers for PVC Plastisol Formulations," pp. 1-6.

* cited by examiner

ENDOTRACHEAL CUFF AND TECHNIQUE FOR USING THE SAME

BACKGROUND OF THE INVENTION

1. Field of the Invention

The present invention relates to medical devices, and more particularly, to airway products, such as tracheal tubes and cuffs.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to control the flow of air, food, fluids, or other substances into and/or out of the patient. For example, medical devices such as tracheal tubes may be used to control the flow of one or more substances into or out of a patient. In many instances it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, tracheal tubes may be used to control the flow of air or other gases through a patient's trachea. Such tracheal tubes may include endotracheal (ET) tubes or tracheostomy tubes. To seal these types of tracheal tubes, an inflatable cuff may be associated with these tubes. When inflated, the cuff generally expands into the surrounding trachea to seal the tracheal passage around the tube.

However, to fit a range of trachea anatomies and to provide low intra cuff pressure, cuff diameters are typically about one and a half times the diameter of the average trachea. Therefore, when inserted in an average-sized trachea, such a cuff is unable to fully expand and will fold in on itself within the trachea. These folds may serve as leak paths that allow mucosal secretions to flow past the cuff and enter the lung. Because mucosal secretions may harbor microbes, it is desirable to prevent such secretions from entering the lungs.

Certain types of cuffs are manufactured from materials that have a lower tendency to form leak paths. For example, high pressure cuffs are typically made of highly elastic materials that may form a relatively smooth seal against the trachea. However, such cuffs have associated disadvantages. Due to their elastic properties, high pressure cuffs are often inflated to at least twice the intracuff pressure of lower pressure cuffs in order to form a sufficient tracheal seal. Such high pressures may cause patient discomfort. Further, the mechanical pressure of the high pressure cuff against the tracheal walls may also cause temporary damage to cilial structures in the trachea that are associated with airway particle clearance.

Other types of cuffs may include swellable layers that may be involved in providing a physical barrier to fill the leak paths. However, such physical barriers may be nonetheless permeable to microbial infiltration. For example, such cuffs may employ a hydrogel that may swell into the folds of the cuff. However, many hydrogel coatings may be too porous to prevent the microbes in mucosal secretions from flowing through leak paths in the cuff. Further, many hydrogel coatings are dynamic in nature, with constantly changing pore sizes.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a medical device that includes an inflatable balloon cuff; and a filtration layer having a pore size of less than 5 microns disposed on a tissue-contacting surface of the balloon cuff.

There is also provided a method of manufacturing a medical device that includes providing an inflatable balloon cuff; and providing a filtration layer having a pore size of less than 5 microns disposed on a tissue-contacting surface of the balloon cuff.

There is also provided a method of sealing a patient's trachea that includes inserting an inflatable balloon cuff into a patient's trachea; applying a monomer solution to a surface of the balloon cuff; and cross-linking the monomer solution to produce a filtration layer having a pore size of less than 5 microns.

There is also provided a medical device that includes: an inflatable balloon cuff; and a filtration layer disposed on a tissue-contacting surface of the balloon cuff, wherein the filtration layer is adapted to filter out microbes from mucosal secretions.

There is also provided a method that includes: filtering out microbes from mucosal secretions before they enter the folds of an inflatable balloon cuff.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1:
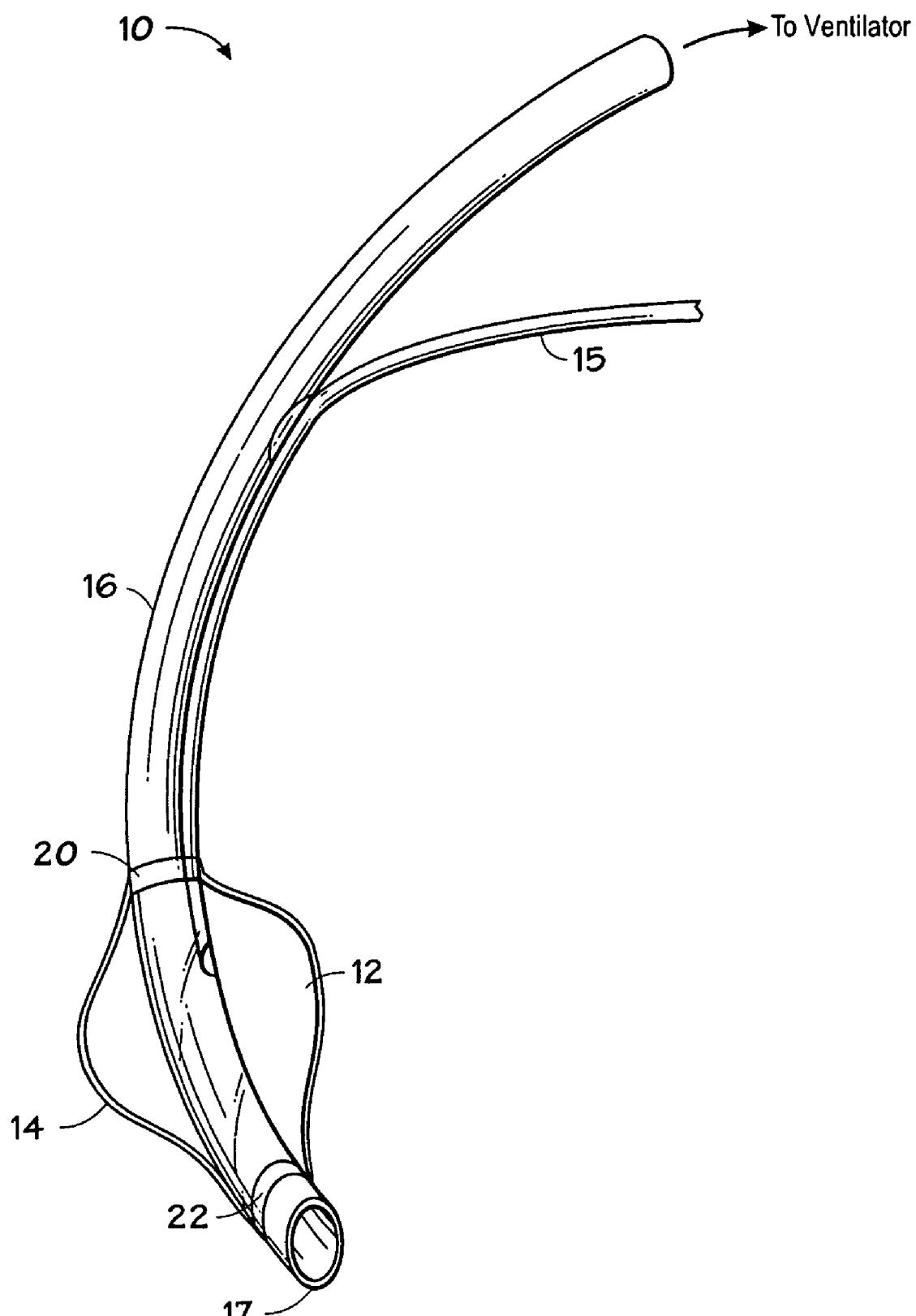
FIG. 1 illustrates an endotracheal tube with an inflatable balloon cuff with a filtration layer in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with some aspects of the present technique, an inflatable cuff is provided that includes a filtration layer that is adapted to filter mucosal secretions before the secretions travel down any folds in the cuff and into the lungs. The filtration layer may be characterized as having a limited pore size that is able to filter out microbes. It is desirable to provide a medical balloon, such as an endotracheal cuff or other medical device, which may substantially seal the passage in which the cuff is inserted so that mechanical ventilation can be used to introduce air, oxygen, or medications into the lungs. As cuffs are typically sized to be larger than the trachea when fully inflated in order to effectively seal a wide range of patient tracheas, the cuff walls are unable to inflate to their maximum diameter and may fold in on themselves, which may cause wrinkles and leak paths to form. These leak paths may be conduits for microbes, for example those found in mucosal secretions, to travel into lungs. The cuffs including filtration layers, as provided herein, may filter out microbes from the mucosal secretions that enter cuff leak paths to travel into the lungs.

A filtration layer may be any suitable material having a pore size smaller than the microbes that are being filtered. As most bacteria have diameters that are microns in scale, a suitable pore size may be on the lower end of the micron scale in order to filter out most bacteria. Many microbes fall into the size range of 0.2-20 microns. In certain embodiments, microbes fall into the size range of 3-5 microns. Exemplary microbes to be filtered include *Puedomonas aeruginosa, Staphylococcus aureus, Enterobacter* spp, *Haemophilus influenza, Streptococcus* spp, *Candida ablicans* (yeast), *Stenotrophomonas multiphilia*, Methicillin Resistant *Staphyloccus aureus*, and others, including viruses. In certain embodiments, an appropriate pore size for the filtration layer is less than 5 microns or less than 2 microns. In other embodiments, the pore size may be less than 0.2 microns in order to filter out the broadest range of microbes. Further, as certain microbes may be capable of changing morphology under pressure in order to "squeeze" through pores having a slightly smaller diameter, a pore size of less than 0.2 microns may be advantageous as such a size may generally be substantially smaller than most bacteria. Pore size may be defined as the average diameter, or a range of diameters, of the individual pores in a membrane. Generally, pore size may be determined statistically by the average dimension of the smallest particle that will pass through the material. Several standardized tests are available to determine pore size. For example, the bubble point test is evaluates performance under aqueous conditions. Pore size may also be calculated from measurements of capillary force, pressure, and water height. One such method is described in ASTM F 316.

The medical cuffs as provided herein may be used in conjunction with any suitable medical device. In certain embodiments, the cuffs as provided herein may be used in conjunction with a catheter, a stent, a feeding tube, an intravenous tube, an endotracheal tube, a tracheostomy tube, a circuit, an airway accessory, a connector, an adapter, a filter, a humidifier, a nebulizer, or a prosthetic, in various embodiments.

An example of a cuff used in conjunction with a medical device is a cuffed endotracheal tube 10, depicted in FIG. 1. The cuffed endotracheal tube 10 includes an inflatable cuff 12 that may be inflated to form a seal against the trachea wall 28 (see FIG. 2). In certain embodiments, the cuff 12 includes a filtration layer 14 that is disposed over the outer surface of the cuff 12. The cuff is disposed on an endotracheal tube 16 that is suitably sized and shaped to be inserted into a patient and allow the passage of air through the endotracheal tube 16. Typically, the cuff is disposed, adhesively or otherwise, towards the distal end 17 of the endotracheal tube 16. The cuff 12 may be inflated and deflated via a lumen 15 in communication with the cuff 12, typically through a hole or notch in the lumen 15. The cuff 12 has a proximal opening 20 and a distal opening 22 formed in the cuff walls sized to accommodate the endotracheal tube 16. The proximal opening 20, located closer to the "machine end" of the tube 16, and a distal opening 22, located closer to the "patient end" of the tube 16, are typically used to mount the cuff 12 to the tube 16.

The cuff 12 may be formed from materials having suitable mechanical properties (such as puncture resistance, pin hole resistance, tensile strength), chemical properties (such as forming a suitable bond to the tube 16), and biocompatibility. In one embodiment, the walls of the inflatable cuff 12 are made of a polyurethane having suitable mechanical and chemical properties. An example of a suitable polyurethane is Dow Pellethane® 2363-80A. In another embodiment, the walls of the inflatable cuff 12 are made of a suitable polyvinyl chloride (PVC). Other suitable materials include polypropylene, polyethylene teraphthalate (PETP), low-density polyethylene (LDPE), silicone, neoprene, or polyisoprene.

Figure 2:
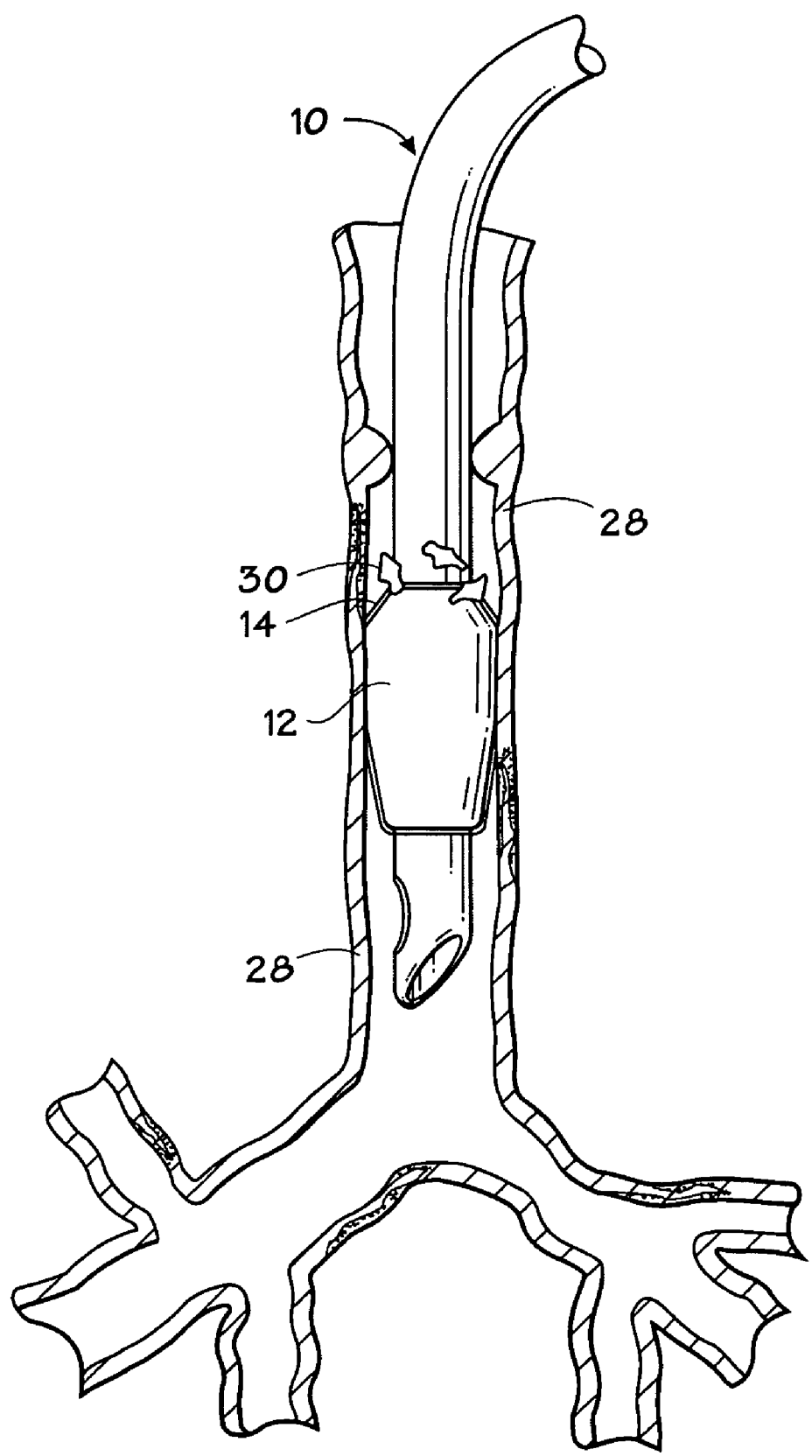
FIG. 2 illustrates the inflatable balloon cuff of the present techniques inserted into a patient's trachea.
Figure 3:
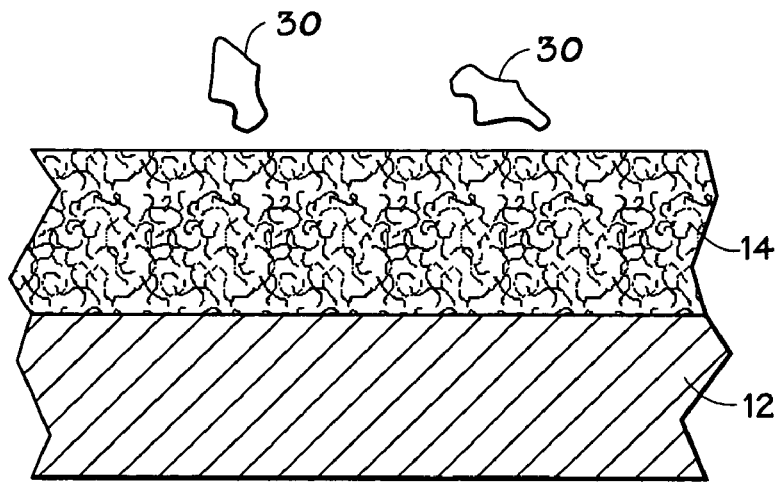
FIG. 3 illustrates a cross-sectional view of the filtration layer applied to an endotracheal cuff.
Figure 4:
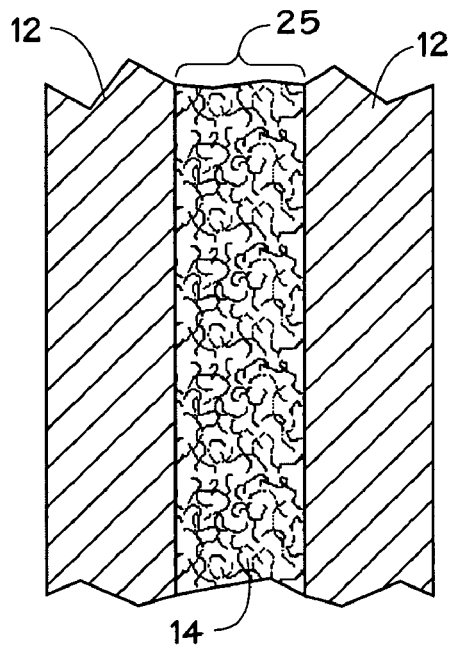
FIG. 4 illustrates an exemplary cuff wrinkle with a filtration layer forming a vertical filtration channel.

The filtration layer 14 is configured to be disposed on the outer, tissue-contacting surface of the cuff 12. The filtration layer 14 reduces or prevents the passage of microbes larger than a certain size. FIG. 2 shows the exemplary cuffed endotracheal tube 10 inserted into a patient's trachea. As depicted, the filtration layer 14 may directly contact mucosal tissue that is involved in producing secretions that may travel into the lungs. The cuff 12 is inflated to form a seal against the tracheal walls 28 such that the filtration layer 14 is in contact with the mucosal tissue. Thus, mucosal secretions 30 encounter the filtration layer 14 before they pass through the trachea into the lungs, as depicted in FIG. 3. The small pore size of the filtration layer 14 prevents the progress of particles larger in the mucosal secretions that are larger than a certain size but still allows the liquid phase to pass through.

Further, the filtration layer 14 may be disposed on the cuff 12 such that as the cuff 12 folds in on itself to form wrinkles 25, the filtration layer 14 creates a vertical channel down the wrinkle 25. In such an embodiment, the filtration layer 14 may be a few microns to several millimeters in thickness in order to fill the fold of the cuff, depending on how the cuff 12 folds. In certain embodiments, it may be advantageous to use a filtration layer 14 that may have a surface treatment or charge, such that the folds of the cuff 12 will be attracted to one another to encourage formation of the vertical channel. For example, a polymer filtration layer 14 may be formed from cross-linked amphipathic polymers such as having hydrophilic branches and a hydrophobic backbone that may adhere easily to a hydrophobic cuff 12. In alternative embodiments, the filtration layer 14 may undergo a surface treatment, such as plasma treatment, in order to modify its surface characteristics. Further, a hydrophilic filtration layer 14 may also encourage formation of a seal of the cuff walls against the mucosal tissue, which is generally hydrophilic in nature.

Figure 5:
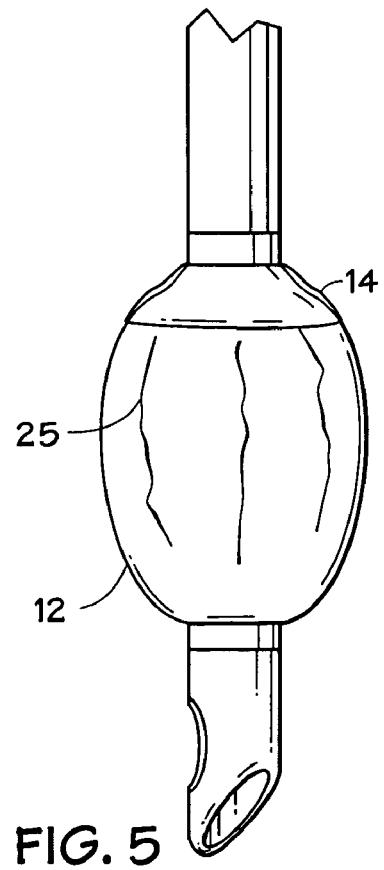
FIG. 5 illustrates an alternative inflatable balloon cuff with a filtration layer disposed on the top of the cuff.

In other embodiments, the filtration layer 14 may be disposed on only a portion of the cuff 12. The filtration layer 14 may be disposed on the cuff such that it creates a barrier to microbial entry into any wrinkles 25. Shown in FIG. 5 is a cuff 12 with a filtration layer 14 disposed on the top of the cuff 12.

Figure 6:
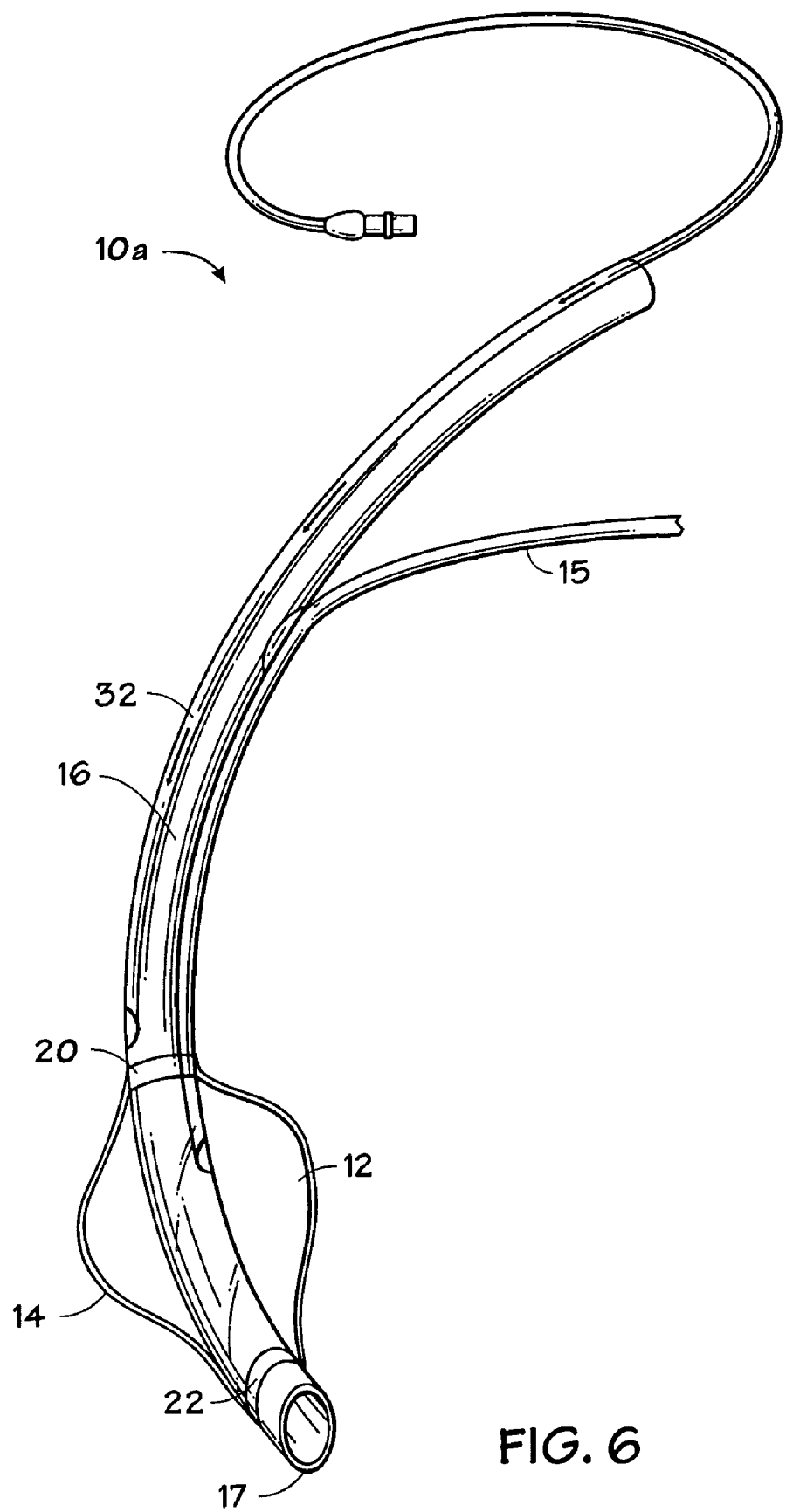
FIG. 6 illustrates a modified endotracheal tube with a lumen adapted to deliver a filtration layer to an inflatable balloon cuff.

When a cuff 12 is inflated into a patient's trachea, the area of the cuff 12 near the proximal opening 20 of the cuff walls may form a relatively flat surface that may tend to collect mucosal secretions. Although these secretions may be periodically aspirated, their collective pressure and weight between aspiration events may tend to accelerate the flow of secretions down the leak paths created by the wrinkles 25. The filtration layer 14 may filter out microbes and larger particles from the secretions before they may enter the wrinkles 14. The filtration layer 14 may be applied to the top of the cuff 12 prior to insertion of the tube 10 into the trachea. Alternatively, the filtration layer may be applied to the cuff 12 after insertion of the tube into the trachea. For example, an endotracheal tube 10a is depicted in FIG. 6. The tube 10a includes a lumen 32 that is adapted to deliver a filtration layer 14 to the area of the cuff 12 near the proximal opening 20. The lumen 32 may also deliver a precursor fluid that may be processed after application to the cuff 12 in order to form the filtration layer 14 in situ. In such an embodiment, the fluid delivered by the lumen 32 should be substantially biocompatible. For example, an amide monomer solution may be delivered through the lumen 32 to the cuff 12 and cross-linked in place by adding a peroxide initiator.

The filtration layer 14 may be any suitable material with an appropriate pore size. For example, the filtration layer 14 may be a microporous polymer or polymer mixture. The pore size of the polymer mixture may be adjusted by increased crosslinking of the polymer. For example, the filtration layer 14 may include a microporous polypropylene blend. Such a microporous polymer may be fabricated by compounding a polypropylene major phase system of less than 15% total weight with a polystyrene minor phase as detailed in "Preparation of Microporous Films from Immiscible Blends via Melt Processing," Chandavasu, et al. Journal of Plastic Film and Sheeting, Vol. 16, No. 4, 288-300 (2000). Alternatively, the filtration layer 14 may be a polyacrylamide polymer network. The acrylamide polymerization solution may be a 4-5% solution (acrylamide/bisacrylamide 19/1) in water/glycerol, with a nominal amount of initiator added. The solution may be polymerized and cross-linked either by ultraviolet radiation or by thermal initiation at elevated temperature. The pore size of the gel may be controlled by changing the amount of crosslinker and the percent of solids in the monomer solution. The cuff 12 may be dipped into the polyacrylamide solution, and removed before initiation of cross-linking. The solution characteristics and dip times may be adjusted, depending on the desired thickness of the filtration layer 14. Polyethyleneimine, polyacrylamide, polymers of dimethylaminoethylmethacrylate, polymers of ammonio methacrylate, and copolymers of dimethylaminoethylmethacrylate and ammonio methacrylate. Alternatively, the filtration layer 14 may be an interpenetrating polymer network, such as a hydrogel network. The pore size of such networks may be controlled through the amount of crosslinking as well as through the monomer or oligomer size.

The filtration layer 14 may also be a homogeneous hydrogel. Such a hydrogel may be polymerized to have the appropriate microporosity through bulk polymerization, i.e. polymerization in the absence of added solvent. Bulk polymerization of a homogeneous hydrogel initially produces a glassy, transparent polymer matrix that is relatively hard. When immersed in water, the glassy matrix swells to become soft and flexible. Although it permits the transfer of water and some low-molecular-weight solutes, such a swollen polymer matrix hydrogel is considered non-porous. The pores between polymer chains are in fact the only spaces available for the mass transfer, and the pore size is within the range of molecular dimensions (a few nanometers or less). Suitable hydrogel monomers may include polyethylene glycol and methacrylic acid.

The distance between crosslinks, or crosslink density, is a critical factor in determining the pore size of a hydrogel "filter". The crosslink density can be controlled by factors such as the crosslinking agent concentration, the molecular weight of the crosslinker, and the state of the hydrogel during the crosslinking process. For instance, the amount the hydrogel is swollen during the crosslinking process will have a large impact on the potential swelling of the final hydrogel. This is due to the distance between the polymer chains under different solvent conditions during the crosslinking process. Because of the high percentage of swelling that occurs in hydrogels, it is possible for hydrogels pressed together to intermingle and achieve molecular entanglement. This helps provide a filtering mechanism in the folds that form along the cuff 12 after inflation within the trachea. In this way, a contiguous microbe filter can be achieved.

In another specific embodiment, the filtration layer 14 may be a layer formed from small peptides with the characteristics of self-assembling into a film, such as those detailed in U.S. Pat. No. 7,098,028. For example, the peptide EAK16 (AEAE-AKAKAEAEAKAK) self-assembles into stable macroscopic membranes in the presence of millimolar concentrations of salt. Peptides having these properties participate in intermolecular interactions which result in the formation and stabilization of beta-sheets at the secondary structure level and interwoven filaments at the tertiary structure level.

A variety of manufacturing techniques can be used to apply the filtration layer 14 to the cuff 12. For example, the cuff 12 can be dipped into a solution containing monomers that may be polymerized on the cuff 12. In other embodiments, the filtration layer 14 may be co-extruded with the cuff 12 or may be molded, co-extrusion blow-molded, electrostatically applied, extruded and applied to a balloon blowing apparatus, or sprayed.

The tracheal cuffs of the present techniques may be incorporated into systems that facilitate positive pressure ventilation of a patient, such as a ventilator. Such systems may typically include connective tubing, a gas source, a monitor, and/or a controller. The controller may be a digital controller, a computer, an electromechanical programmable controller, or any other control system.

Typically, endotracheal cuffs are inflated within a patient's trachea such that the intra cuff pressure is approximately 20-25 cm $H_2O$. Endotracheal cuffs utilizing inflation pressures significantly greater 50 cm $H_2O$ may be referred to as high-pressure cuffs, while cuffs that are able to effectively seal the trachea at pressures less than 30 cm $H_2O$ may be considered low-pressure cuffs. In certain embodiments, intra cuff inflation pressures of 10-30 cm $H_2O$ may be used with the cuffs of the present techniques.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:
1. A medical device comprising:
    an inflatable balloon cuff;

a tracheal tube associated with the balloon cuff, wherein the tracheal tube passes through an opening of the balloon cuff; and a filtration layer having a pore size of less than 5 microns disposed on a tissue-contacting surface of the balloon cuff.

2. The medical device, as set forth in claim 1, wherein the filtration layer has a pore size of less than 0.2 microns.

3. The medical device, as set forth in claim 1, wherein the filtration layer is at least 0.0002 inches in thickness.

4. The medical device, as set forth in claim 1, wherein the balloon cuff comprises polyethylene teraphthalate (PETP), low-density polyethylene (LDPE), polyvinyl chloride (PVC), silicone, neoprene, polyisoprene, or polyurethane (PU).

5. The medical device, as set forth in claim 1, comprising a ventilator to which the endotracheal tube is operatively connected.

6. The medical device, as set forth in claim 1, wherein the filtration layer is cross-linked.

7. The medical device, as set forth in claim 1, wherein filtration layer comprises a hydrogel.

8. The medical device, as set forth in claim 1, wherein the filtration layer comprises an interpenetrating polymer network.

9. The medical device, as set forth in claim 1, wherein the filtration layer comprises a peptide protein network.

10. The medical device, as set forth in claim 1, wherein the filtration layer comprises at least one of polyethyleneimine, polyacrylamide, dimethylaminoethylmethacrylate, ammonio methacrylate, or any combination thereof.

11. A method of manufacturing a medical device, comprising:
providing an inflatable balloon cuff;
providing an endotracheal tube associated with the balloon cuff, wherein the endotracheal tube passes through an opening of the balloon cuff; and
providing a filtration layer having a pore size of less than 5 microns disposed on a tissue-contacting surface of the balloon cuff.

12. The method, as set forth in claim 11, wherein providing the filtration layer comprises providing a layer at least 0.0002 inches in thickness.

13. The method, as set forth in claim 11, comprising providing a ventilator to which the endotracheal tube is operatively connected.

14. The method, as set forth in claim 11, wherein providing the filtration layer comprises providing a cross-linked layer.

15. The method, as set forth in claim 11, wherein providing the filtration layer comprises providing a hydrogel.

16. The method, as set forth in claim 11, wherein providing the filtration layer comprises providing an interpenetrating polymer network.

17. The method, as set forth in claim 11, wherein providing the filtration layer comprises providing a protein network.

18. The method, as set forth in claim 11, wherein providing the filtration layer comprises providing at least one of polyethyleneimine, polyacrylamide, dimethylaminoethylmethacrylate, ammonio methacrylate, or any combination thereof.

19. A method of sealing a patient's trachea, comprising:
inserting an inflatable balloon cuff into a patient's trachea;
applying a monomer solution to a surface of the balloon cuff; and
cross-linking the monomer solution to produce a filtration layer having a pore size of less than 5 microns.

20. The method, as set forth in claim 19, wherein cross-linking the monomer solution comprises UV radiation.

21. The method, as set forth in claim 19, wherein cross-linking the monomer solution comprises heat cross-linking.

22. A medical device comprising:
an inflatable balloon cuff;
an endotracheal tube associated with the balloon cuff, wherein the endotracheal tube passes through an opening of the balloon cuff; and
a filtration layer disposed on a tissue-contacting surface of the balloon cuff, wherein the filtration layer is adapted to filter out microbes from mucosal secretions.

23. A method comprising:
filtering out microbes from mucosal secretions before they enter the folds of an inflatable balloon cuff associated with an endotracheal tube, wherein the endotracheal tube passes through a proximal opening and a distal opening of the balloon cuff.

24. The medical device, as set forth in claim 1, wherein the tracheal tube comprises an endotracheal tube.

25. A medical device comprising:
an inflatable balloon cuff;
a tracheal tube associated with the balloon cuff, wherein the tracheal tube passes through an opening of the balloon cuff; and
a filtration layer disposed on a tissue-contacting surface of the balloon cuff, wherein the filtration layer is adapted to filter out microbes from mucosal secretions.

* * * * *